(12) United States Patent
Elzein et al.

(10) Patent No.: US 7,488,720 B2
(45) Date of Patent: Feb. 10, 2009

(54) A₁ ADENOSINE RECEPTOR AGONISTS

(75) Inventors: Elfatih Elzein, Fremont, CA (US); Xiaofen Li, Mountain View, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 118 days.

(21) Appl. No.: 11/546,658

(22) Filed: Oct. 11, 2006

(65) Prior Publication Data

US 2007/0087994 A1 Apr. 19, 2007

Related U.S. Application Data

(60) Provisional application No. 60/726,616, filed on Oct. 13, 2005.

(51) Int. Cl.
- *A01N 43/04* (2006.01)
- *A61K 31/70* (2006.01)
- *C07H 19/00* (2006.01)
- *C07H 19/167* (2006.01)
- *C07H 19/173* (2006.01)

(52) U.S. Cl. .................. 514/46; 514/45; 536/27.1; 536/27.13; 536/27.3; 536/27.6; 536/27.62

(58) Field of Classification Search .................. None
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,023,252 | A | 6/1991 | Hseih |
| 5,616,345 | A | 4/1997 | Geoghegan et al. |
| 6,326,359 | B1 * | 12/2001 | Monaghan et al. ............ 514/46 |
| 2003/0013675 | A1 * | 1/2003 | Yeadon et al. ................. 514/46 |

FOREIGN PATENT DOCUMENTS

| | | | |
|---|---|---|---|
| WO | WO 00/23457 | A1 | 4/2000 |
| WO | WO 02/094273 | A2 | 11/2002 |
| WO | WO 03/014137 | A1 | 2/2003 |
| WO | WO 2004/069185 | A2 | 8/2004 |

OTHER PUBLICATIONS

Ohno et al., "Modulation of adenosine receptor afinity and intrinsic efficacy in adenine nucleosides substituted at the 2-position", Bioorganic and Medicinal Chemistry, vol. 12, 2004, 2995-3007.*
Dhalla et al., "Pharmacology and Therapeutic Applications of A1 Adenosine Receptor Ligands", Current Topics in Medicinal Chemistry, 3(4) 369-385, 2003.*
Adenosine A₂B Receptors as Therapeutic Targets, Feoktistov et al., Trends Pharmacol Sci 19:148-153, Apr. 1998.
B. Lerman et al. *Cardiac Electrophysiology of Adenosine* Circulation, vol. 83 (1991), p. 1499-1509.
J. C. Shryock et al. *Adenosine and Adenosine Receptors in the Cardiovascular System: Biochemistry, Physiology, and Pharmacology* The Am. J. Cardiology, vol. 79 (1997) p. 2-10.
E. A. van Schaick et al. *Physiological Indirect Effect Modeling of the Antilipolytic Effects of Adenosine A1-Receptor Agonists* J. Pharmacokinetics and Biopharmaceutics, vol. 25 (1997) p. 673-694.
P. Strong *Suppression of Non-asterified Fatty Acids and Triacylglycerol in Experiental Animals by the Adenosine Analogue* Clinical Science vol. 84 (1993) p. 663-669.
Thiebaud et al. *Effect of Long Chain Triglyceride Indusion on Glucose Metabolism in Man* Metab. Clin. Exp. vol. 31 (1982) p. 1128-1136.
G. Boden et al. *Mechanisms of Fatty Acid-Induced Inhibition of Glucose Uptake* J. Clin. Invest. vol. 93 (1994) p. 2438-2446.
P. J. Randle et al *The Glucose Fatty-acid Cycle* The Lancet (1963) p. 785-789.
R. B. Clark et al. *Partial Agonists and G Protein-coupled Receptor Desensitization* TiPS, vol. 20 (1999) p. 279-286.
Gierschik et al., *Signal Amplification in HL-60 Granulocytes* 1991 p. 725-732.
Gierschik et al., *Contribution of Nucleoside Diphosphokinase to Guanine Nucleotide Regulation of Agonist Binding to Formyl Peptide Receptors* 1991 p. 17-23.
Lorenzen et al., *Affinity of Central Adenosine A1 Receptors is Decreased in Spontaneously Hypertensive Rats* 1993 p. 223-230.
Traynor & Nahorski, *Mosulation by u-Opioid Agonists of Guanosine-5'-O-(3-[35S]thio)triphosphate Binding to Membranes from Human Neuroblastoma SH-SY-5Y5Y Cells* 1995 p. 848-854.

* cited by examiner

*Primary Examiner*—Traviss C McIntosh, III
(74) *Attorney, Agent, or Firm*—Michael J. Beck

(57) ABSTRACT

Disclosed are novel compounds that are A₁ adenosine receptor agonists, useful for treating various disease states, in particular tachycardia and atrial flutter, angina, diseases related to release of nonesterified fatty acids, and myocardial infarction.

13 Claims, No Drawings

$A_1$ ADENOSINE RECEPTOR AGONISTS

Priority is claimed to U.S. Provisional Patent Application Ser. No. 60/726,616, filed Oct. 13, 2005, the complete disclosure of which is hereby incorporated by reference.

FIELD OF THE INVENTION

The present invention relates to novel compounds that are $A_1$ adenosine receptor agonists, and to their use in treating mammals for various disease states, including modifying cardiac activity, in particular treatment of arrhythmia. The compounds are also useful for treating CNS disorders, diabetic disorders, obesity, and modifying adipocyte function. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148-153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499-1509 and J. C. Shryock and L. Belardinelli The Am. J. Cardiology, Vol. 79 (1997) P 2-10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli Circulation, Vol. 83 (1991), P 1499-1509 and J. C. Shryock and L. Belardinelli, Am. J. Cardiology, Vol. 79 (1997) P 2-10.

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biopharmaceutics, Vol. 25 (1997) p 673-694 and P. Strong Clinical Science Vol. 84 (1993) p. 663-669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128-1136 and G. Boden et al J. Clin. Invest. Vol. 93 (1994) p 2438-2446). The hypothesis of a glucose fatty acid cycle was proposed by P. J. Randle as early as 1963 (P. J. Randle et al Lancet (1963) p. 785-789). A tenet of this hypothesis would be that limiting the supply of fatty acids to the peripheral tissues should promote carbohydrate utilization (P. Strong et al Clinical Science Vol. 84 (1993) p. 663-669).

Adenosine itself has proven effective in treating disease states related to the $A_1$ adenosine receptor, for example in terminating paroxysmal supraventricular tachycardia. However, the effects of adenosine are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

Accordingly, one object of this invention is to provide compounds that are $A_1$ adenosine receptor agonists with a half life greater than that of adenosine, and that are selective for the $A_1$ adenosine receptor. Additionally, it has been found that $A_1$ adenosine receptor agonists that do not penetrate the blood-brain barrier potentially have fewer side effects. Accordingly, another object of this invention is to provide compounds that are $A_1$ adenosine receptor agonists with a half life greater than that of adenosine, are selective for the $A_1$ adenosine receptor, and do not penetrate the blood barrier.

SUMMARY OF THE INVENTION

Accordingly, in a first aspect, the invention relates to compounds of Formula I:

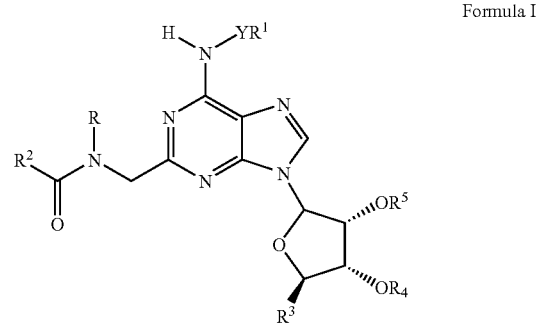

Formula I wherein:
R is hydrogen or lower alkyl;
$R^1$ is optionally substituted alkyl, optionally substituted cycloalkyl, optionally substituted aryl, optionally substituted heterocyclyl, or optionally substituted heteroaryl;
$R^2$ is optionally substituted alkyl, optionally substituted cycloalkyl, optionally substituted aryl; optionally substituted heteroaryl, or optionally substituted heterocyclyl;

$R^3$ is —$CH_2OR^6$ or —$C(O)NR^7R^8$; in which $R^6$ is hydrogen or acyl, and $R^7$ and $R^8$ are independently hydrogen or lower alkyl;

$R^4$ and $R^5$ are independently hydrogen or acyl; and

Y is a covalent bond or optionally substituted alkylene;

and the pharmaceutically acceptable salts thereof.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with a partial or full selective $A_1$ receptor agonist. Such diseases include atrial fibrillation, supraventricular tachycardia and atrial flutter, congestive heart failure, antilipolytic effects in adipocytes, epilepsy, stroke, diabetes, obesity, ischemia, including stable angina, unstable angina, cardiac transplant, and myocardial infarction.

A fourth aspect of this invention relates to preferred compounds of Formula I that do not penetrate the blood-brain barrier, and consequently have no CNS effect. Such preferred compounds include compounds of Formula I in which R is hydrogen, $R^1$ is cycloalkyl of 3-6 carbon atoms, $R^2$ is alkyl substituted by —$SO_3H$, or cycloalkyl substituted by —$SO_3H$, or aryl substituted by —$SO_3H$; or heteroaryl substituted by —$SO_3H$, or heterocyclyl substituted by —$SO_3H$, and $R^3$ is —$CH_2OH$, particular where $R^4$ and $R^5$ are hydrogen and Y is a covalent bond.

Within this class of compounds, one preferred group includes compounds in which $R^2$ is alkyl substituted by —$SO_3H$ or aryl substituted by —$SO_3H$. Within this group, one preferred subgroup includes those compounds in which $R^2$ is alkyl of 1-4 carbon atoms substituted by —$SO_3H$, particularly where $R^2$ is —$CH_2SO_3H$, and more particularly where $R^1$ is cyclopentyl. Another preferred subgroup included compounds in which $R^2$ is phenyl substituted by —$SO_3H$, particularly 4-benzenesulfonic acid, more particularly where $R^1$ is cyclopentyl.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-ecyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —$SO_2$-alkyl, $SO_2$-aryl, —$SO_2$-heteroaryl, and $SO_3H$. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-5 atoms or groups independently chosen from oxygen, sulfur and —$NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "lower alkylene" refers to a diradical of a branched or unbranched saturated hydrocarbon chain having from 1 to 6 carbon atoms.

The term "substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or (2) an alkylene group as defined above that is interrupted by 1-5 atoms or groups independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1-20 atoms as defined above. Examples of substituted alkylenes are chloromethylene (—CH(Cl)—), aminoethylene (—$CH(NH_2)CH_2$—), methylaminoethylene (—CH(NHMe)$CH_2$—), 2-carboxypropylene isomers(—$CH_2CH(CO_2H)CH_2$—), ethoxyethyl (—$CH_2CH_2O$—

CH₂CH₂—), ethylmethylaminoethyl (—CH₂CH₂N(CH₃) CH₂CH₂—), 1-ethoxy-2-(2-ethoxy-ethoxy)ethane (—CH₂CH₂O—CH₂CH₂—OCH₂CH₂—OCH₂CH₂—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH₂), 1-propylene or allyl (—CH₂CH═CH₂), isopropylene (—C(CH₃)═CH₂), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)ₙR, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH₃), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl,-SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)ₙR, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF₃, amino, substituted amino, cyano, or —S(O)ₙR, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF₃, amino, substituted amino, cyano, or —S(O)ₙR, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF₃, amino, substituted amino, cyano, or —S(O)ₙR, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)ₙR, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl,. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —$S(O)_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxynitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

The compounds of Formula I include the definition that "R and $YR^1$ when taken together with the nitrogen atom to which they are attached represents optionally substituted heterocyclyl". Such a definition includes heterocycles with only nitrogen in the ring, for example pyrrolidines and piperidines, and also includes heterocycles that have more than one heteroatom in the ring, for example piperazines, morpholines, and the like.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, phosphate, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2$R, in which R is alkyl, aryl, or heteroaryl. "Substituted sulfone" refers to a group —$S(O)_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and hydrates and prodrugs of such compounds.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-lkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279-286), and less likely to cause side effects.

Nomenclature

The naming and numbering of the compounds of the invention is illustrated with a representative compound of Formula I in which R is hydrogen, $R^1$ is 2-hydroxycycloalkyl, $R^2$ is hydrogen, $R^3$ is 2-fluorophenyl, $R^4$ and $R^5$ are both hydrogen, and X and Y are both covalent bonds:

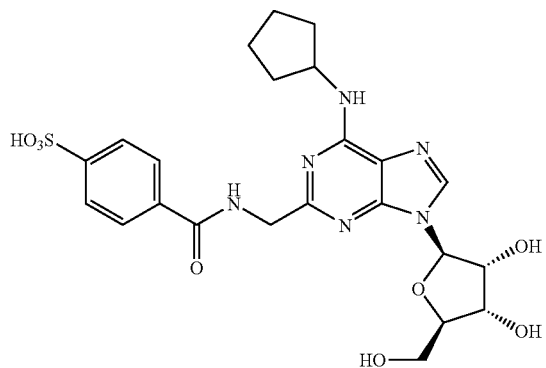

which is named:
4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

One synthetic scheme for preparing the compounds of Formula I starts with a compound of formula (4), the preparation of which is shown in Reaction Scheme I:

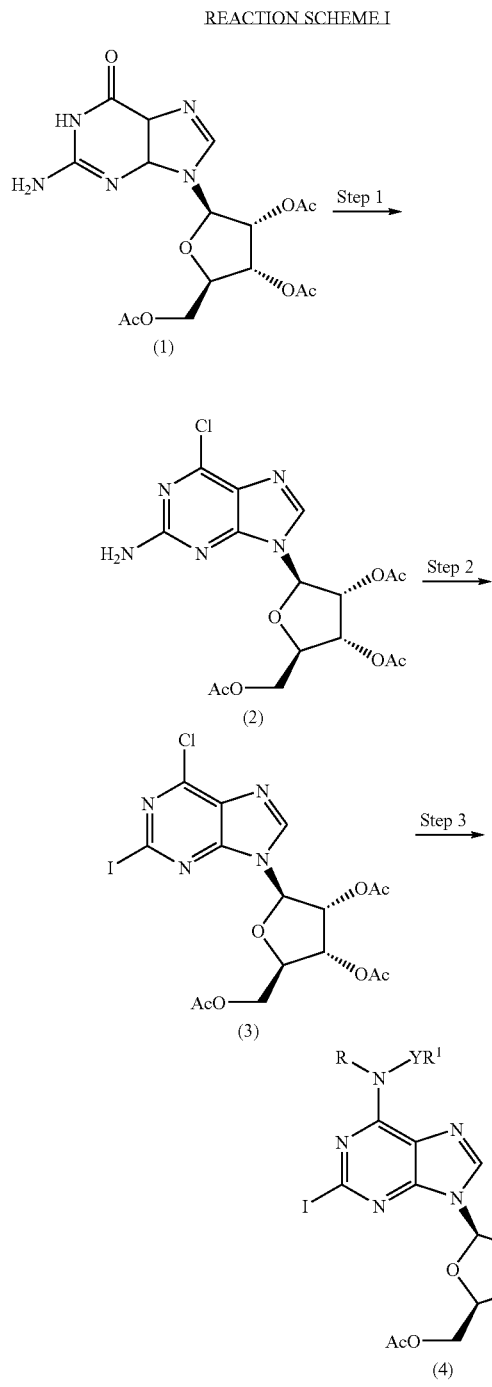

Step 1—Preparation of a Compound of Formula (2)

The compound of formula (1), triacetylguanosine, is commercially available, or may be prepared by methods well known in the art. The compound of formula (2) is prepared from the compound of formula (1) conventionally, for example by reaction with a chlorinating agent, for example phosphorus oxychloride, in an inert solvent, for example acetonitrile, in the presence of a quaternary ammonium salt, for example tetraethylammonium chloride, and a hindered base, for example N,N-dimethylaniline. The reaction is conducted at a temperature of about 40-100° C., preferably about 85° C., for about 1-12 hours, preferably about 2 hours. When the reaction is substantially complete, the product ((2R,3R, 4R,5R)-4-acetyloxy-5-(acetyloxymethyl)-2-(2-amino-6-chloropurin-9-yl)oxolan-3-yl acetate, the compound of formula (2)) is isolated by conventional means and purified by chromatography.

Step 2—Preparation of a Compound of Formula (3)

The compound of formula (2) is converted to (2R,3R,4R, 5R)-4-acetyloxy-5-(acetyloxymethyl)-2-(6-chloro-2-iodopurin-9-yl)oxolan-3-yl acetate, the compound of formula (3), by reaction with amyl nitrite in the presence of diiodomethane. The reaction is conducted in an inert solvent, for example acetonitrile, at a temperature of about 40-100° C., preferably about 80° C., for about 4-24 hours, preferably about 18 hours. When the reaction is substantially complete, the product of formula (3) is isolated by conventional means, for example removal of the solvent under reduced pressure and purifying the residue by chromatography.

Step 3—Preparation of a Compound of Formula (4)

The compound of formula (3) is converted to a compound of formula (4) bby reaction with an amine of formula $R^1NH_2$. In general, the reaction is conducted in an inert solvent, for example N,N-dimethylformamide, in the presence of a hindered amine, for example diisopropylethylamine, at a temperature of about 1 5-30° C., preferably about 25° C., for about 4-24 hours, preferably about 18 hours. When the reaction is substantially complete, the product of formula (4) is isolated by conventional means, for example removal of the solvent under reduced pressure and purifying the residue by chromatography.

The compounds of formula (4) are converted to a compound of Formula I as shown in Reaction Scheme II.

REACTION SCHEME II

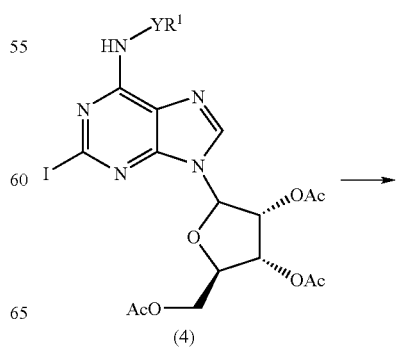

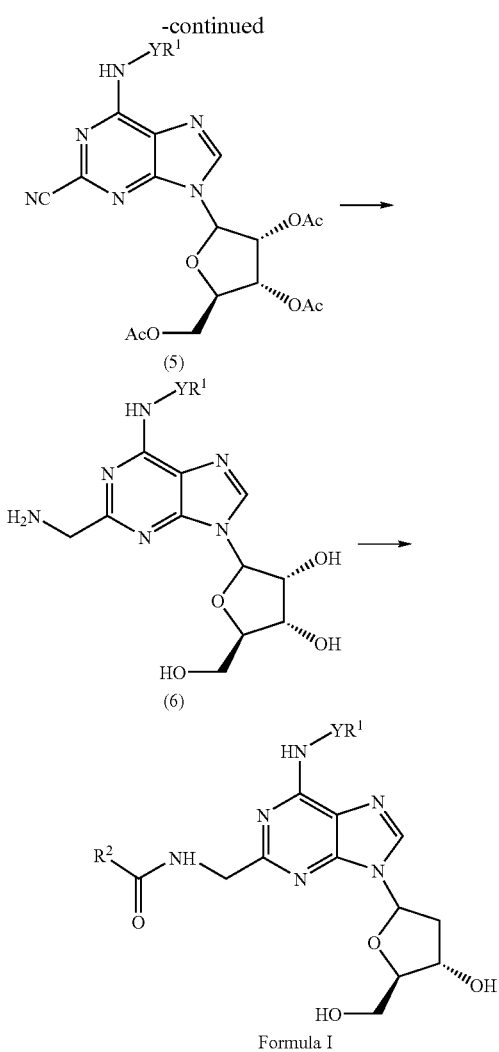

Formula I

Step 1—Preparation of Formula (5)

The compound of formula (5) is prepared conventionally from the compound of formula (4), for example by reaction of (4) with tributyltincyanide in the presence of tetrakis(triphenylphosphine)palladium in an inert solvent, for example N,N-dimethylformamide. The reaction is conducted at a temperature of about 100-120° C., preferably about 120° C., for about 4-24 hours, preferably about 18 hours. When the reaction is substantially complete, the product of formula (5) is isolated by conventional means and purified, for example by chromatography.

Step 2—Preparation of Formula (6)

The compound of formula (6) is prepared from the compound of formula (5) by reaction with a reducing agent, for example by reaction with hydrogen in the presence of a metal catalyst, for example Raney nickel. The reaction is conducted in an inert solvent, for example methanol, at room temperature for about 2 hours. When the reaction is substantially complete, the product of formula (6) is isolated by conventional means and purified, for example by chromatography.

Step 3—Preparation of a Compound of Formula I

The compound of formula (6) is then converted to a compound of Formula I by reaction with a carboxylic acid of the formula $R^2CO_2H$ or a salt of the carboxylic acid. For example, reaction of a metal salt of the formula $R^2CO_2K$ with the compound of formula (6) in the presence of a carbodiimide derivative, for example 1(3-dimethylaminopropyl)-3-ethylcarbodiimide. The reaction is conducted in an inert solvent, for example a mixture of water and N,N-dimethylformamide, at about room temperature, for about 1-10 hours, preferably about 4 hours. When the reaction is substantially complete, the product of Formula I is isolated by conventional means, and purified, for example by chromatography.

Utility, Testing and Administration

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure, non-insulin-dependent diabetes mellitus, hyperglycemia, epilepsy (anticonvulsant activity), and neuroprotection. $A_1$ agonists also have antilipolytic effects in adipocytes that leads to a decreased release of nonesterified fatty acids.

Testing

Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

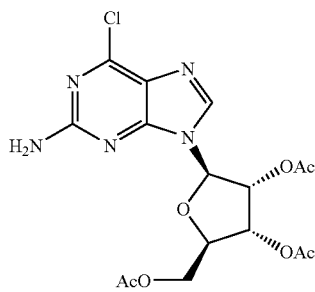

(2)

To a solution of 2',3',5'-triacetylguanosine (4.0 g, 9.78 mmol) and tetraethylammonium chloride (4.9 g, 29.3 mmol) in acetonitrile (60 ml) was added N,N-dimethylaniline (1.85 ml, 14.67 mmol), followed by phosphorus oxychloride (7.28 ml, 78 mmol). The resulting solution was refluxed for 2 hours, after which the solvent was removed under reduced pressure. The residue was diluted with methylene chloride, washed with aqueous saturated sodium bicarbonate, and the organic layer dried over sodium sulfate. The solvent was removed under reduced pressure, and the residue chromatographed on silica gel, eluting with 4% methanol/methylene chloride, to provide (2R,3R,4R,5R)-4-acetyloxy-5-(acetyloxymethyl)-2-(2-amino-6-chloropurin-9-yl)oxolan-3-yl acetate, the compound of formula (2). $^1$H NMR (CDCl$_3$) was satisfactory.

EXAMPLE 2

Preparation of a Compound of Formula (3)

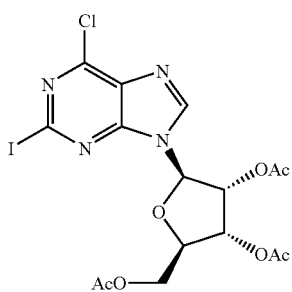

(3)

To a solution of (2R,3R,4R,5R)-4-acetyloxy-5-(acetyloxymethyl)-2-(2-amino-6-chloropurin-9-yl)oxolan-3-yl acetate (3.8 g, 8.88 mmoles) in acetonitrile (40 ml) was added diiodomethane (3.4 ml) and n-amyl nitrite (8.2 ml). The resulting mixture was refluxed overnight, then the solvent removed under reduced pressure. The residue was chromatographed on silica gel, eluting with a mixture of 40% ethanol/ 60% hexane, to provide (2R,3R,4R,5R)-4-acetyloxy-5-(acetyloxymethyl)-2-(6-chloro-2-iodopurin-9-yl)oxolan-3-yl acetate (2.7 g) as a light yellow solid.

EXAMPLE 3

Preparation of a Compound of Formula (4)

A. Preparation of a Compound of Formula (4) in which R$^1$ is Cyclopentyl and Y is a Covalent Bond

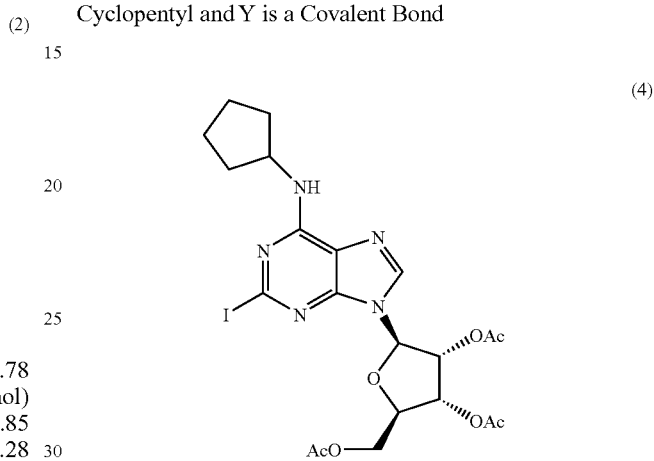

(4)

To a solution of (2R,3R,4R,5R)-4-acetyloxy-5-(acetyloxymethyl)-2-(6-chloro-2-iodopurin-9-yl)oxolan-3-yl acetate (1.15 g, 2.13 mmol) in N,N-dimethylformamide (20 ml) was added cyclopentylamine (0.42 ml, 4.26 mmol) and diisopropylethylamine (10 ml), and the mixture was stirred at room temperature overnight. The solvent was removed under reduced pressure, and the residue chromatographed on a silica gel column, eluting with a mixture of 40% ethanol/60% hexane, to provide (2R,3R,4R,5R)-4-acetyloxy-2-(acetyloxymethyl)-5-[6-(cyclopentylamino)-2-iodopurin-9-yl]oxolan-3-yl acetate (0.9 g), a compound of formula (4).

B. Preparation of a Compound of Formula (4) varying R$^1$ and Y

Similarly, following the procedure of 3A above, but replacing cyclopentylamine with other amines of formula R$^1$YNH$_2$, other compounds of formula (4) are prepared, for example:

(2R,3R,4R,5R)-4-acetyloxy-2-(acetyloxymethyl)-5-[6-(cyclohexylamino)-2-iodopurin-9-yl]oxolan-3-yl acetate;

(2R,3R,4R,5R)-4-acetyloxy-2-(acetyloxymethyl)-5-[6-(n-hexylamino)-2-iodopurin-9-yl]oxolan-3-yl acetate;

(2R,3R,4R,5R)-4-acetyloxy-2-(acetyloxymethyl)-5-[6-(anilino)-2-iodopurin-9-yl]oxolan-3-yl acetate;

(2R,3R,4R,5R)-4-acetyloxy-2-(acetyloxymethyl)-5-[6-(benzylamino)-2-iodopurin-9-yl]oxolan-3-yl acetate;

(2R,3R,4R,5R)-4-acetyloxy-5-(acetyloxymethyl)-2-[2-iodo-6-(oxolan-3-ylamino)purin-9-yl]oxolan-3-yl acetate; and (2R,3R,4R,5R)-4-acetyloxy-2-(acetyloxymethyl)-5-[6-(pyrid-2-ylamino)-2-iodopurin-9-yl]oxolan-3-yl acetate.

EXAMPLE 4

Preparation of a Compound of Formula (5)

A. Preparation of a Compound of Formula (5) in which $R^1$ is Cyclopentyl and Y is a Covalent Bond

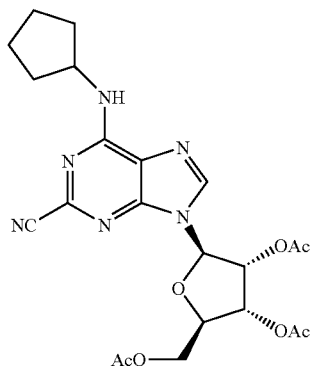

(5)

To a solution of (2R,3R,4R,5R)-4-acetyloxy-2-(acetyloxymethyl)-5-[6-(cyclopentylamino)-2-iodopurin-9-yl]oxolan-3-yl acetate (0.9 g, 1.53 mmol) in N,N-dimethylformamide (40 ml) was added tributyltin cyanide (0.58 g, 1.84 mmol) and tetrakis(triphenylphosphine)palladium (0.27 g, 0.23 mmol), and the mixture was stirred at 120° C. f overnight. Solvent was removed under reduced pressure, and the residue was dissolved in ethyl acetate and filtered through celite. The solvent was removed under reduced pressure, and the residue was chromatographed on silica gel, eluting with a mixture of ethanol/hexane 1:1, to provide (2R,3R,4R,5R)-4-acetyloxy-2-(acetyloxy-methyl)-5-[2-cyano-6-(cyclopentylamino)purin-9-yl]oxolan-3-yl acetate (0.65 g).

B. Preparation of a Compound of Formula (5) varying $R^1$ and Y

Similarly, following the procedure of 4A above, but replacing (2R,3R,4R,5R)-4-acetyloxy-2-(acetyloxymethyl)-5-[6-(cyclopentylamino)-2-iodopurin-9-yl]oxolan-3-yl acetate with other compounds of formula (4), other compounds of formula (5) are prepared, for example:

(2R,3R,4R,5R)-4-acetyloxy-2-(acetyloxymethyl)-5-[6-(cyclohexylamino)-2-cyanopurin-9-yl]oxolan-3-yl acetate;

(2R,3R,4R,5R)-4-acetyloxy-2-(acetyloxymethyl)-5-[6-(n-hexylamino)-2-cyanopurin-9-yl]oxolan-3-yl acetate;

(2R,3R,4R,5R)-4-acetyloxy-2-(acetyloxymethyl)-5-[6-(anilino)-2-cyanopurin-9-yl]oxolan-3-yl acetate;

(2R,3R,4R,5R)-4-acetyloxy-2-(acetyloxymethyl)-5-[6-(benzylamino)-2-cyanopurin-9-yl]oxolan-3-yl acetate;

(2R,3R,4R,5R)-4-acetyloxy-5-(acetyloxymethyl)-2-[2-cyano-6-(oxolan-3-ylamino)purin-9-yl]oxolan-3-yl acetate; and (2R,3R,4R,5R)-4-acetyloxy-2-(acetyloxymethyl)-5-[6-(pyrid-2-ylamino)-2-cyanopurin-9-yl]oxolan-3-yl acetate.

EXAMPLE 5

Preparation of a Compound of Formula (6)

A. Preparation of a Compound of Formula (6) in which $R^1$ is Cyclopentyl and Y is a Covalent Bond

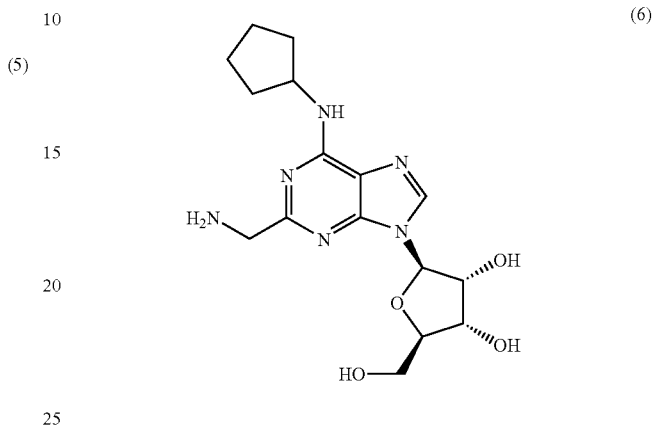

(6)

A. To a solution of (2R,3R,4R,5R)-4-acetyloxy-2-(acetyloxy-methyl)-5-[2-cyano-6-(cyclopentylamino)purin-9-yl]oxolan-3-yl acetate (0.3 g) in methanol was added Raney nickel, and the mixture was stirred under hydrogen at 40 psi for 2 hours at room temperature. The catalyst was filtered off through celite, washed with methanol, and solvent removed from the filtrate under reduced pressure. The residue was crystallized from a mixture of methanol and hexane, to provide (4S,2R,3R,5R)-2-[2-(aminomethyl)-6-(cyclopentylamino)purin-9-yl]-5-(hydroxymethyl)oxolane-3,4-diol.

B. Preparation of a Compound of Formula (6) varying $R^1$ and Y

Similarly, following the procedure of 5A above, but replacing (2R,3R,4R,5R)-4-acetyloxy-2-(acetyloxy-methyl)-5-[2-cyano-6-(cyclopentylamino)purin-9-yl]oxolan-3-yl acetate with other compounds of formula (5), other compounds of formula (6) are prepared, for example:

(4S,2R,3R,5R)-2-[2-(aminomethyl)-6-(cyclohexylamino)purin-9-yl]-5-(hydroxymethyl)oxolane-3,4-diol;

(4S,2R,3R,5R)-2-[2-(aminomethyl)-6-(hexylamino)purin-9-yl]-5-(hydroxymethyl)oxolane-3,4-diol;

(4S,2R,3R,5R)-2-[2-(aminomethyl)-6-(anilino)purin-9-yl]-5-(hydroxymethyl)oxolane-3,4-diol;

(4S,2R,3R,5R)-2-[2-(aminomethyl)-6-(benzylamino)purin-9-yl]-5-(hydroxymethyl)oxolane-3,4-diol;

(4S,2R,3R,5R)-2-[2-(aminomethyl)-6-(oxolan-3-ylamino)purin-9-yl]-5-(hydroxymethyl)oxolane-3,4-diol; and (4S,2R,3R,5R)-2-[2-(aminomethyl)-6-(pyrid-2-ylamino)purin-9-yl]-5-(hydroxymethyl)oxolane-3,4-diol.

EXAMPLE 6

Preparation of a Compound of Formula I

A. Preparation of a Compound of Formula I in which R is Hydrogen, $R^1$ is Cyclopentyl, $R^2$ is 4-Sulfobenzoic Acid, and Y is a Covalent Bond

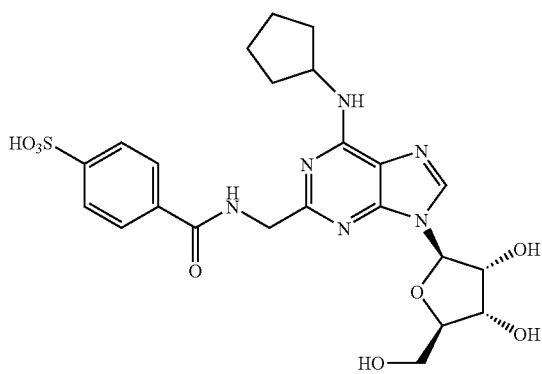

To a solution of (2R,3R,4R,5R)-4-acetyloxy-5-(acetyloxymethyl)-2-[2-(aminomethyl)-6-(cyclopentylamino)purin-9-yl]oxolan-3-yl acetate (55 mg, 0.15 mmol) in a mixture of N,N-dimethylformamide (5 ml) and water (10 ml) was added 4-sulfobenzoic acid (37 mg, 0.153 mmol) and 1(3-dimethylaminopropyl)-3-ethylcarbodiimide (28 mg, 0.147 mmol), and the mixture was stirred for 4 hours. Solvent was removed under reduced pressure, and the residue was purified by HPLC, to provide 4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid (39 mg). MS MH+548.57.

$^1$H NMR (400 MHz, CD$_3$OD) δ: 1.52-1.57 (m, 2H), 1.72-1.76 (m, 2H), 1.83-1.90 (m, 2H), 1.95-2.01 (m, 2H), 3.72 (dd, 1H, J=3.2, 12.6 Hz), 3.85 (dd, 1H, J=2.4, 12.6 Hz), 4.14-4.16 (m, 1H), 4.29-4.31 (m, 1H), 4.50 (s, 2H), 4.78-4.81 (m, 1H), 5.94 (d, 1H, J=6.2 Hz), 7.94 (d, 2H J=8.2 Hz), 8.00 (d, 2H, J=8.6 Hz), 8.19 (s, 1)

$K_{iA1}$=5 nm

B. Preparation of a Compound of Formula I in which R is Hydrogen, R$^1$ is Cyclopentyl, R$^2$ is 2-Sulfoacetic Acid, and Y is a Covalent Bond Similarly, following the procedure of 6A above, but replacing 4-sulfobenzoic acid with 2-sulfoacetic acid ethane, the following compounds of Formula I was prepared:

N-({9-[(4S,2R,3R,5R)-3,4-dihydroxy-5-(hydroxymethyl)oxolan-2-yl]-6-(cyclopentylamino)purin-2-yl}methyl)carbamoylmethylsulfonic acid; MS MH+486.5.

$^1$H NMR (400 MHz, CD$_3$OD) δ: 1.56-1.64 (m, 2H), 1.69-1.83 (m, 4H), 2.1-2.18 (m, 2H), 3.17-3.21 (m, 1H), 3.76 (dd, 1H, J=3.2, 12.6 Hz), 3.85 (s, 2H), 3.92 (dd, 1H, J=2.8, 12.2 Hz), 4.15-4.17 (m, 1H), 4.37-4.39 (m, 1H), 4.51 (s, 2H), 4.72-4.84 (m, 1H,), 5.95 (d, 1H, J=5.6 Hz), 8.21 (s, 1H).

C. Preparation of a Compound of Formula I, varying R, R$^1$, R$^2$, and Y

Similarly, following the procedure of 6A above, but optionally replacing (2R,3R,4R,5R)-4-acetyloxy-5-(acetyloxymethyl)-2-[2-(aminomethyl)-6-(cyclopentylamino)purin-9-yl]oxolan-3-yl acetate with other compounds of formula (6), and optionally replacing 4-sulfobenzoic acid with other compounds of formula R$^2$CO$_2$H, other compounds of Formula I are prepared, for example:

4-[N-({9-[(4S,2R,3R,5R)-3,4-dihydroxy-5-(hydroxymethyl)oxolan-2-yl]-6-(cyclohexylamino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(n-hexylamino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(anilino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(benzylamino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(oxolan-3-ylamino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(pyrid-2-ylamino)purin-2-yl}methyl)carbamoyl]benzenesulfonic acid;

4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid;

N-({9-[(4S,2R,3R,5R)-3,4-dihydroxy-5-(hydroxymethyl)oxolan-2-yl]-6-(cyclopentylamino)purin-2-yl}methyl)benzamide;

N-({9-[(4S,2R,3R,5R)-3,4-dihydroxy-5-(hydroxymethyl)oxolan-2-yl]-6-(cyclopentylamino)purin-2-yl}methyl)-3-pyridylcarboxamide;

N-({9-[(4S,2R,3R,5R)-3,4-dihydroxy-5-(hydroxymethyl)oxolan-2-yl]-6-(cyclopentylamino)purin-2-yl }methyl)cyclopentylcarboxamide;

4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid; and 4-[N-({9-[(4S,2R,3R,5R)-3,4-dihydroxy-5-(hydroxymethyl)oxolan-2-yl]-6-(cyclopentylamino)purin-2-yl}methyl)-N-methylcarbamoyl]benzenesulfonic acid.

D. Preparation of a Compound of Formula I, varying R, R$^1$, R$^2$, and Y

Similarly, following the procedure of 6A above, but optionally replacing (2R,3R,4R,5R)-4-acetyloxy-5-(acetyloxymethyl)-2-[2-(aminomethyl)-6-(cyclopentylamino)purin-9-yl]oxolan-3-yl acetate with other compounds of formula (6), and optionally replacing 4-sulfobenzoic acid with other compounds of formula R$^2$CO$_2$H, any compound of Formula I is prepared.

EXAMPLE 7

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
| --- | --- |
| Active Ingredient | 25.0 |
| Cellulose, microcrystalline | 200.0 |

-continued

| Ingredient | Quantity (mg/tablet) |
| --- | --- |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
| --- | --- |
| Active Ingredient | 5.0 mg |
| Corn Oil | 1.0 mL |

EXAMPLE 14

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 15

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |

-continued

| Ingredients | grams |
|---|---|
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 16

Sustained Release Composition

| Ingredient | Weight Range (%) | Preferred Range (%) | Most Preferred |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 17

Binding Assays—$DDT_1$ Cells

Cell Culture

DDT cells (hamster vas deferens smooth muscle cell line) are grown as monolayers in petri dishes using Dulbecco's Modified Eagle's Medium (DMEM) containing 2.5 µg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells are subcultured twice weekly by dispersion in Hank's Balanced Salt Solution (HBSS) without the divalent cations and containing 1 mM EDTA. The cells are then seeded in growth medium at a density of $1.2 \times 10^5$ cells per plate and experiments are performed 4 days later at approximately one day preconfluence.

Membrane Preparations

Attached cells are washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension is then centrifuged at 27,000×g for 10 min. The pellet is resuspended in homogenization buffer by vortexing and centrifuged as described above. The final pellet is resuspended in 1 vol of 50 mM Tris-HCl buffer pH 7.4 containing 5 mM $MgCl_2$ for $A_1$ AdoR assays. For the [$^{35}$S]GTPγS binding assay the final pellet is resuspended in 50 mM Tris-HCl pH 7.4 containing 5 mM $MgCl_2$, 100 mM NaCl and 1 mM dithiothreitol. This membrane suspension is then placed in liquid nitrogen for 10 min, thawed and used for assays. The protein content is determined with a Bradford™ Assay Kit using bovine serum albumin as standard.

Competitive Binding Assay

Pig striatum are prepared by homogenation in 50 mM Tris buffer (5× volume of tissue mass pH=7.4). After centrifugation at 19,000 rpm for 25 minutes at 4° C., the supernatant is discarded, and the process repeated twice. Compounds of Formula I are assayed to determine their affinity for the $A_1$ receptor in a pig striatum membrane preparation or a $DDT_1$ membrane prep. Briefly, 0.2 mg of pig striatal membranes or $DDT_1$ cell membranes are treated with adenosine deaminase and 50 mM Tris buffer (pH=7.4) followed by mixing. To the pig membranes is added 2 µL of serially diluted DMSO stock solution of the compounds of this invention at concentrations ranging from 100 microM to 10 nM. The control receives 2 microL of DMSO alone, then the antagonist [$^3$H]8-cyclopentylxanthine (CPX) for pig striatum or the agonist [$^3$H]2-chloro-6-cyclopentyladenosine (CCPA) for $DDT_1$ membranes in Tris buffer (50 mM, pH of 7.4) is added to achieve a final concentration of 2 nM. After incubation at 23° C. for 2 hours, the solutions are filtered using a membrane harvester using multiple washing of the membranes (3×). The filter disks are counted in scintillation cocktail affording the amount of displacement of tritiated CPX or by the competitive binding of compounds of Formula I.

The compounds of Formula I are shown to be of high, medium, or low affinity for the $A_1$ adenosine receptor in this assay.

EXAMPLE 18

[$^{35}$S]GTPγS Binding Assays $A_1$-agonist stimulated [$^{35}$S]GTPγS binding is determined by a modification of the method described by Gierscikik et al.

(1991) and Lorenzen et al. (1993). Membrane protein (30-50 μg) is incubated in a volume of 0.1 ml containing 50 mM Tris-HCl buffer pH 7.4, 5 mM $MgCl_2$, 100 mM NaCl, 1 mM dithiothreitol, 0.2 units $ml^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding is determined by the addition of 10 μM GTPγS. Agonist stimulated binding is determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 μM GDP gave the optimal stimulation of CPA dependent [$^{35}$S]GTPγS binding and this concentration was therefore used in all studies. In saturation experiments, 0.5 nM [$^{35}$S]GTPγS is incubated with 0.5-1000 nM GTPγS. At the end of the incubation, each suspension is filtered and the retained radioactivity determined as described above.

The compounds of Formula I are shown to be partial or full agonists of the $A_1$ adenosine receptor in this assay.

EXAMPLE 21 cAMP Assay

A scintillation proximity assay (SPA) using rabbit antibodies directed at cAMP using an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, $DDT_1$ cells are cultured in clear bottomed 96 well microtiter plates with opaque wells at concentrations between $10^4$ to $10^6$ cells per well in 40 μl of HBSS at 37° C. (5% $CO_2$ and 95% humidity). The partial or full $A_1$ agonists (5 μl) of this invention are incubated at various concentrations with the $DDT_1$ cells in the presence of rolipram (50 μM), and 5 μM forskolin for 10 min at 37° C. The cells are immediately lysed by treatment 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) is added to each well followed by sealing the plate. After 15-20 hours at 23° C., the amount of bound [$^{125}$I] cAMP to the fluoromicrospheres is determined by counting in a microtitre plate scintillation counter for 2 minutes. Comparison of counts with standard curves generated for cAMP using a similar protocol affords the cAMP present after cell lysis.

The compounds of Formula I are shown to be functionally active as $A_1$ agonists with a partial or full decrease in cAMP in this assay.

EXAMPLE 22

Blood Brain Penetration Assay

Studies of transport of the compounds of Formula I were carried out in accordance with an in situ brain perfusion technique disclosed in "Methods in Molecular medicine, Vol. 89, pp209-218, by Quentin R. Smith and David D. Allen Procedures:

Animals

Anesthesia: Cocktail of 90 mg/kg ketamine/9 mg/kg xylazine was given at a volume of 1 mg/kg as i.m. injection.

Surgery and perfusion: The left common carotid artery was cannulated, the chest opened and the heart severed. The brain was perfused at 10 ml/min for a predetermined duration of time, followed by post-perfusion with perfusion solution for 30 seconds.

B. Test Drugs

Dose Preparation

A stock solution of the test drug was prepared as a solution of 1 nM in DMSO.

| | Study Design | | | |
|---|---|---|---|---|
| Compound | Nr of animals | Dose conc (μM) | Perfusion Duration (min) | Brain region collected |
| Test compound | 3 | 5 | 1 | Left cerebrum |

C. Treatment
1. Three rats per group were infused with the study compounds or a control compound via the left common carotid artery.
2. Brain and perfusion solution samples were obtained at the end of the perfusions.

D. Sample Collection
1. Brains were collected and the left hemispheres or regions thereof were segmented and flash frozen in liquid nitrogen.
2. A sample of the perfusion solution was also taken after each perfusion into an Eppendorf tube, and stored at −80° C. in separate container from the brain samples.
3. When necessary, prior to the perfusion, blood samples were collected in tubes prepared with study anticoagulant. Whole blood was centrifuged at 8000 rpm for 3 minutes. Plasma was collected into Eppendorf tubes and frozen at −80° C. in separate container from the brain samples.

E. Analytical and Data Analysis

Concentrations of study and marker compounds in all samples was measured using LC/MS-MS (and/or LC-UV technique when applicable) and permeability kinetics were determined.

Results

Chlorpromazine was used as a control, and was shown to penetrate the blood brain barrier at the rate of 61.5 pmol/g second.

In contrast, 4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid was seen to penetrate the blood brain barrier at the rate of 0.015 61.5 pmol/g second; and N-({9-[(4S,2R,3R,5R)-3,4-dihydroxy-5-(hydroxymethyl)oxolan-2-yl]-6-(cyclopentylamino)purin-2-yl}methyl)carbamoylmethylsulfonic acid at the rate of 0.10 61.5 pmol/g second.

Accordingly, the compounds are shown to be functionally active as $A_1$ agonists that do not penetrate the blood brain barrier.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound of Formula I:

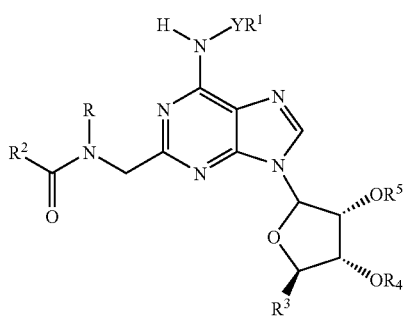

Formula I wherein:
R is hydrogen or lower alkyl;
$R^1$ is alkyl, cycloalkyl, aryl, heterocyclyl, or heteroaryl;
$R^2$ is alkyl substituted by —$SO_3H$, cycloalkyl substituted by —$SO_3H$, aryl substituted by —$SO_3H$, heteroaryl substituted by —$SO_3H$, or heterocyclyl substituted by —$SO_3H$;
$R^3$ is —$CH_2OR^6$ or —$C(O)NR^7R^8$; in which $R^6$ is hydrogen or acyl, and $R^7$ and $R^8$ are independently hydrogen or lower alkyl;
$R^4$ and $R^5$ are independently hydrogen or lower alkyl; and
Y is a covalent bond or alkylene;
or a pharmaceutically acceptable salt thereof.

2. The compound of claim 1, wherein:
R is hydrogen;
$R^1$ is cycloalkyl of 3-6 carbon atoms;
$R^2$ is alkyl substituted by —$SO_3H$, cycloalkyl substituted by —$SO_3H$, aryl substituted by —$SO_3H$; heteroaryl substituted by —$SO_3H$, or heterocyclyl substituted by —$SO_3H$; and
$R^3$ is —$CH_2OH$.

3. The compound of claim 2, wherein $R^4$ and $R^5$ are hydrogen; and Y is a covalent bond.

4. The compound of claim 3, wherein $R^2$ is alkyl substituted by —$SO_3H$ or aryl substituted by —$SO_3H$.

5. The compound of claim 4, wherein $R^2$ is alkyl of 1-4 carbon atoms substituted by —$SO_3H$.

6. The compound of claim 5, wherein $R^1$ is cyclopentyl.

7. The compound of claim 6, wherein $R^2$ is —$CH_2SO_3H$, namely N-({9-[(4S,2R,3R,5R)-3,4-dihydroxy-5-(hydroxymethyl)oxolan-2-yl]-6-(cyclopentylamino)purin-2-yl}methyl)carbamoylmethylsulfonic acid.

8. The compound of claim 4, wherein $R^2$ is phenyl substituted by —$SO_3H$.

9. The compound of claim 8, wherein $R^1$ is cyclopentyl.

10. The compound of claim 9, wherein $R^2$ is 4-benzenesulfonic acid, namely 4-[N-({9-[(4S,2R,3R,5R)-3,4-dihydroxy-5-(hydroxymethyl)oxolan-2-yl]-6-(cyclopentylamino)purin-2-yl}methyl)carbamoyl]benzenesulfonic acid.

11. A method of agonizing an $A_1$ adenosine receptor in a mammal, comprising administering to a mammal in need thereof a therapeutically effective dose of a compound of claim 1.

12. The method of claim 11, wherein the mammal has a disease state chosen from atrial fibrillation, supraventricular tachycardia and atrial flutter, congestive heart failure, epilepsy, stroke, diabetes, obesity, ischemia, stable angina, unstable angina, cardiac transplant, and myocardial infarction.

13. A pharmaceutical composition comprising at least one pharmaceutically acceptable excipient and a therapeutically effective amount of a compound of claim 1.

* * * * *